(12) United States Patent
Labombarbe et al.

(10) Patent No.: US 10,543,121 B2
(45) Date of Patent: Jan. 28, 2020

(54) CONTROLLED RELEASE CONTAINER

(71) Applicant: Amcor Rigid Plastics USA, LLC, Wilmington, DE (US)

(72) Inventors: Chris Labombarbe, Ypsilanti, MI (US); Bradley Wilson, Manchester, MI (US); Richard Steih, Jackson, MI (US); Elizabeth D. Maczek, Westminster, CO (US); Kirk Edward Maki, Tecumseh, MI (US)

(73) Assignee: AMCOR RIGID PLASTICS USA, LLC, Wilmington, DE (US)

( * ) Notice: Subject to any disclaimer, the term of this patent is extended or adjusted under 35 U.S.C. 154(b) by 275 days.

(21) Appl. No.: 15/301,243

(22) PCT Filed: Mar. 30, 2015

(86) PCT No.: PCT/US2015/023363
§ 371 (c)(1),
(2) Date: Sep. 30, 2016

(87) PCT Pub. No.: WO2015/153469
PCT Pub. Date: Oct. 8, 2015

(65) Prior Publication Data
US 2017/0020726 A1    Jan. 26, 2017

Related U.S. Application Data

(60) Provisional application No. 61/972,645, filed on Mar. 31, 2014.

(51) Int. Cl.
*A61F 9/00* (2006.01)
*B65D 1/02* (2006.01)
(Continued)

(52) U.S. Cl.
CPC .......... *A61F 9/0008* (2013.01); *B65D 1/0261* (2013.01); *B65D 1/08* (2013.01); *B65D 1/42* (2013.01); *B65D 83/0094* (2013.01)

(58) Field of Classification Search
CPC ....... A61F 9/0008; B65D 1/0261; B65D 1/08; B65D 47/18; B65D 1/42; B65D 83/0094
See application file for complete search history.

(56) References Cited

U.S. PATENT DOCUMENTS 3,409,167 A   11/1968  Blanchard
3,473,524 A   10/1969  Drewe
(Continued)

FOREIGN PATENT DOCUMENTS

EP   2489604 A1   8/2012
GB   480489 A    2/1938
(Continued)

OTHER PUBLICATIONS

Supplementary European Search Report dated Oct. 30, 2017 in corresponding European Patent Application 15773918 (9 pages).
(Continued)

*Primary Examiner* — Adam Marcetich
*Assistant Examiner* — Jessica R Arble
(74) *Attorney, Agent, or Firm* — Harness, Dickey & Pierce, P.L.C.

(57) ABSTRACT

A controlled release container including a base. The base has a flexible diaphragm movable between a relaxed position and a depressed position. In the depressed position the flexible diaphragm reduces an interior volume of the container to dispense a dosage amount of material stored within the container. The dosage amount directly corresponds to an internal volume of the container displaced by moving the flexible diaphragm to the depressed position.

9 Claims, 12 Drawing Sheets

(51) Int. Cl.
    *B65D 83/00*     (2006.01)
    *B65D 1/08*     (2006.01)
    *B65D 1/42*     (2006.01)

(56) References Cited

U.S. PATENT DOCUMENTS

| | | | |
|---|---|---|---|
| 5,085,651 A | | 2/1992 | Py |
| 5,163,929 A | * | 11/1992 | Py .................. A61F 9/0008 604/294 |
| 5,624,057 A | | 4/1997 | Lifshey |
| 5,673,822 A | * | 10/1997 | Chalmin ............ A61F 9/0008 222/183 |
| 5,680,952 A | * | 10/1997 | Chasteen ............ B65D 17/08 220/268 |
| 5,775,546 A | * | 7/1998 | Buehler .............. B01L 3/021 222/209 |
| 6,336,571 B1 | * | 1/2002 | Chibret ............ A61F 9/0008 222/189.09 |
| 7,451,886 B2 | | 11/2008 | Lisch et al. |
| 2005/0211795 A1 | | 9/2005 | Ueda et al. |
| 2006/0108378 A1 | * | 5/2006 | Cohen ................ A61F 9/0008 222/211 |
| 2006/0138074 A1 | * | 6/2006 | Melrose ............ B65D 1/0276 215/373 |
| 2007/0093765 A1 | | 4/2007 | Kawashiro et al. |
| 2008/0110336 A1 | * | 5/2008 | Cresswell .......... F04B 43/0054 92/98 R |
| 2009/0230152 A1 | * | 9/2009 | Decottignies ...... A45D 40/0075 222/319 |
| 2010/0016814 A1 | | 1/2010 | Gokhale et al. |
| 2011/0017700 A1 | * | 1/2011 | Patcheak ............ B65D 1/0276 215/381 |
| 2011/0253738 A1 | * | 10/2011 | Mileti ............ B05B 11/00412 222/1 |
| 2012/0325828 A1 | * | 12/2012 | Houlton ............ B65D 79/005 220/600 |
| 2013/0213980 A1 | | 8/2013 | Pedmo et al. |
| 2013/0220968 A1 | * | 8/2013 | Imai .................. B65D 1/0261 215/371 |

FOREIGN PATENT DOCUMENTS

| | | |
|---|---|---|
| WO | WO-9729020 A1 | 8/1997 |
| WO | WO-0108993 A1 | 2/2001 |
| WO | WO-2004009457 A1 | 1/2004 |
| WO | WO-2011055114 A2 | 5/2011 |
| WO | WO-2013/033550 A2 | 3/2013 |

OTHER PUBLICATIONS

International Search Report and Written Opinion of the ISA for PCT/US2015/023363, ISA/KR, Daejeon, dated Jun. 25, 2015.
Opposition dated Jun. 28, 2017 in corresponding Colombian Patent Application NC2016/0002713.

\* cited by examiner

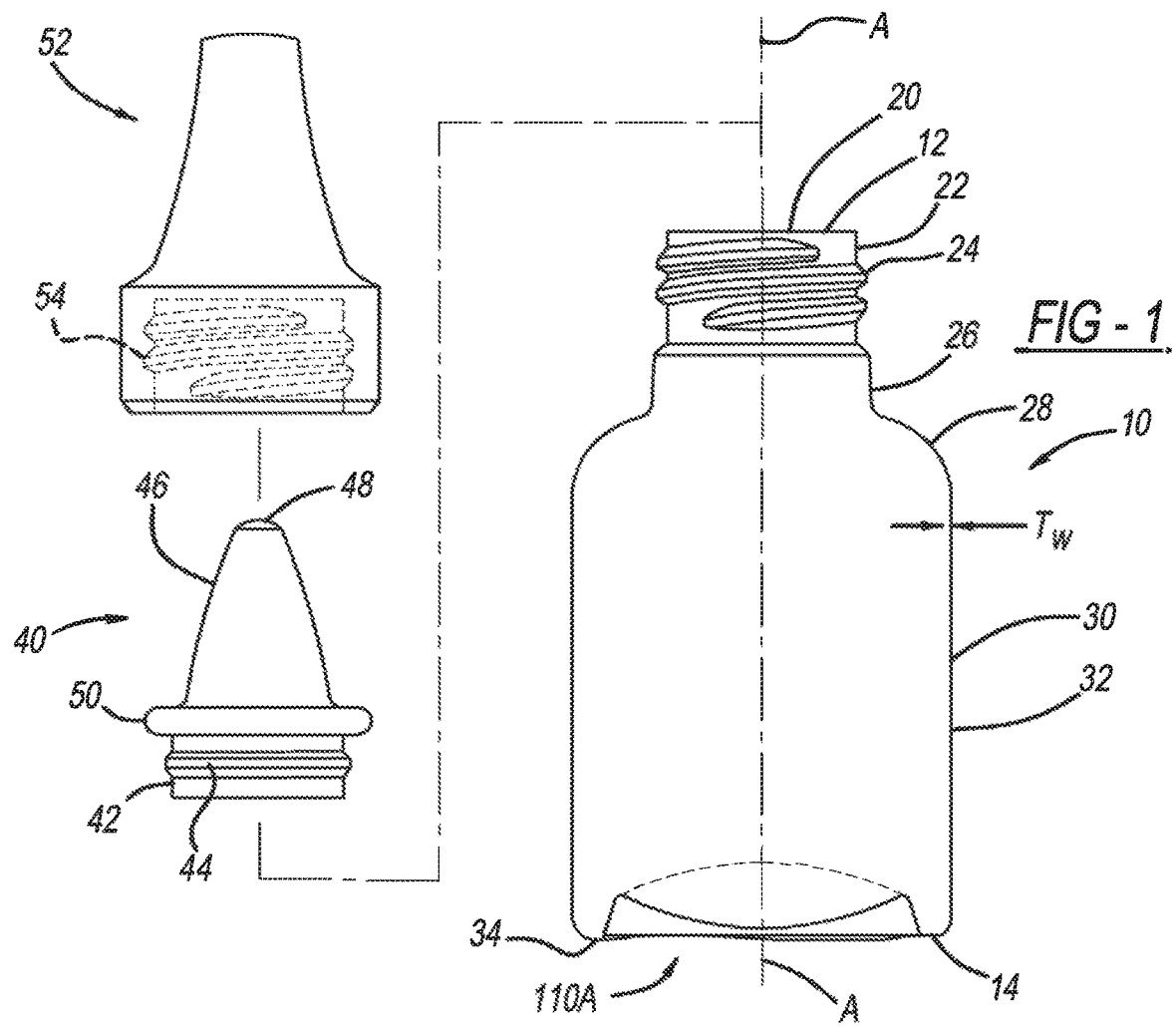
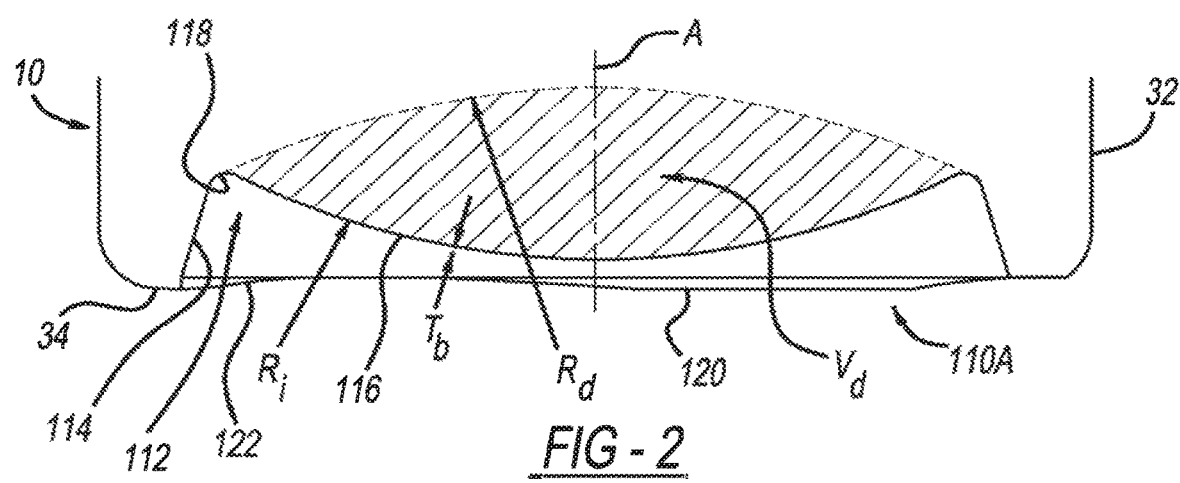

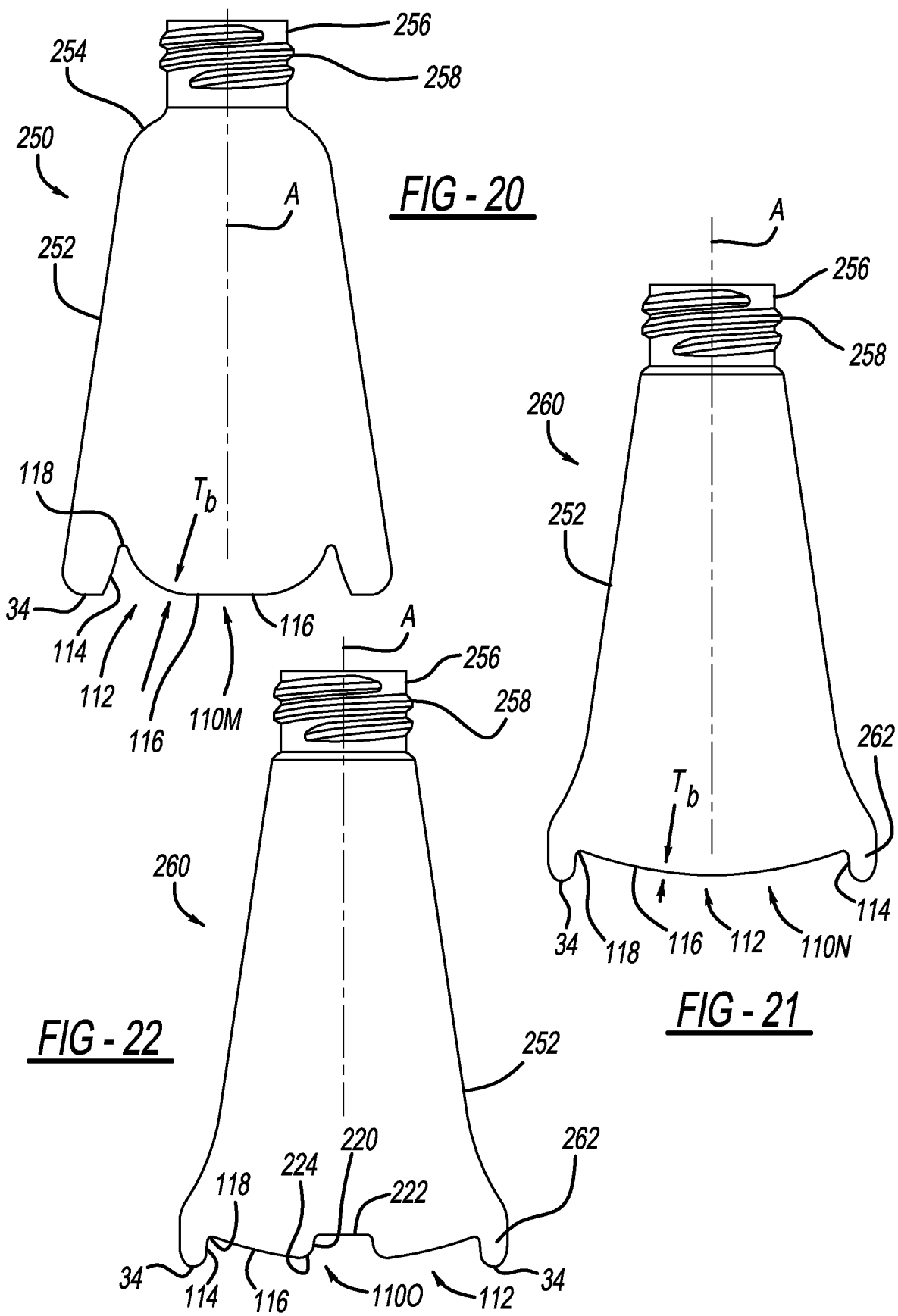

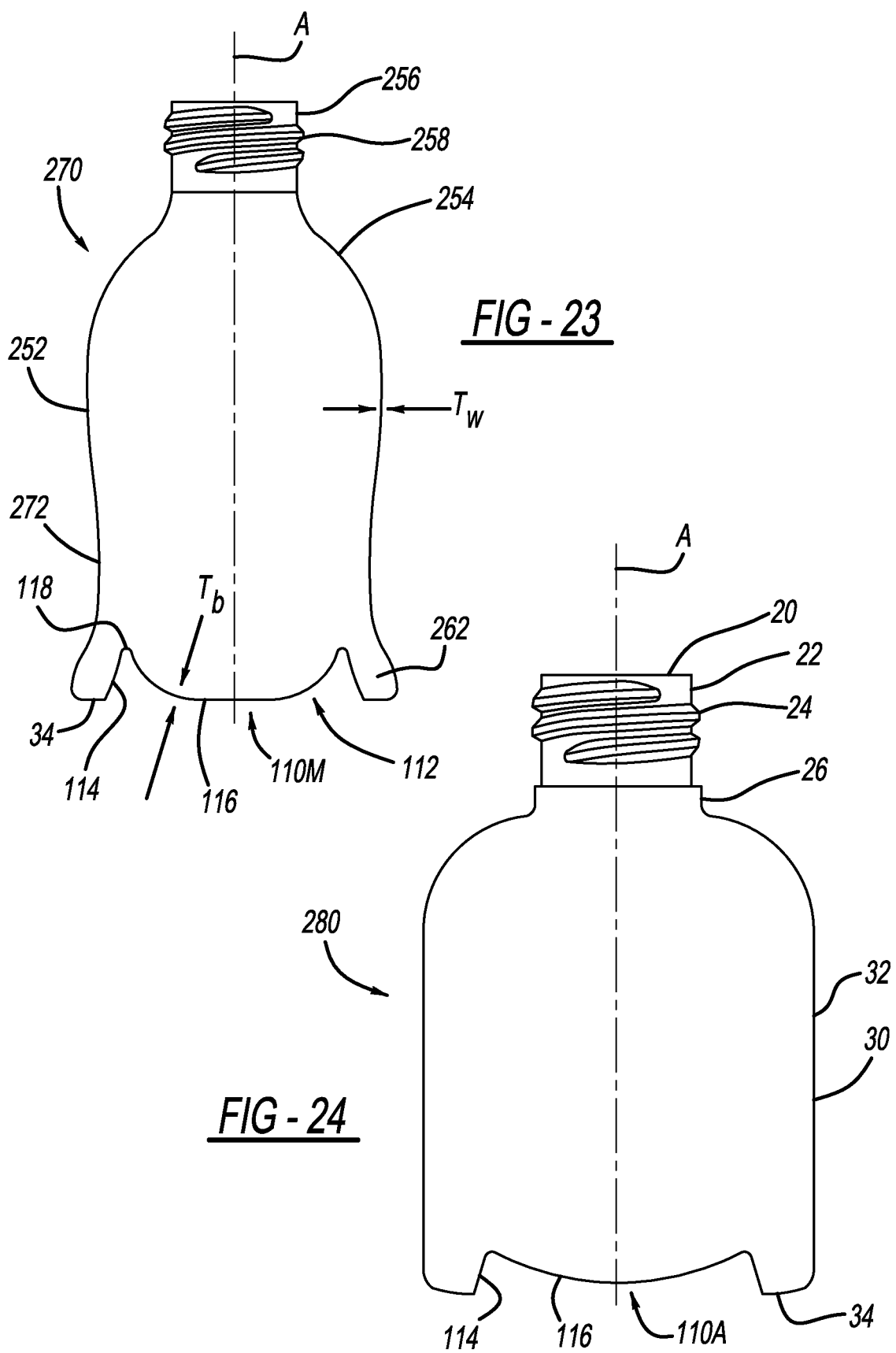

CONTROLLED RELEASE CONTAINER

CROSS-REFERENCE TO RELATED APPLICATION

This application claims the benefit of U.S. Provisional Application No. 61/972,645 filed Mar. 31, 2014, the entire disclosure of which is incorporated herein by reference.

FIELD

The present disclosure relates to a controlled release fluid dispensing system, such as a drop or stream dispensing bottle system.

BACKGROUND

This section provides background information related to the present disclosure, which is not necessarily prior art.

Existing containers that provide for controlled release of a product contained therein are subject to various disadvantages. For example, the controlled release is often provided by a multipiece pump, which is typically costly, complex to assemble, and subject to failure. Other containers have flexible sidewalls, which when pressed inward provide for a release that may be inconsistent, difficult to measure, and difficult to direct or deposit.

Ophthalmic containers are exemplary dropper containers including a dropper tip and flexible sidewalls. The containers are typically round or oval, and usually dispense by squeezing the container sides while the container is inverted to release one or more drops as needed. A closure is usually fastened to the container and can have child resistant or tamper evident features.

Existing controlled release dosing containers and methods often undesirably require dosing by way of a secondary dosing vehicle, and have various other disadvantages. For example, using a tablespoon to measure a dosage is often not very accurate. Using a syringe, eyedropper, dosage cup, or dosing spoon requires use of a secondary item for accuracy, requires a complex two-part system, can potentially result in contamination of the dosage, and can increase costs. Improved controlled release containers that do not experience the disadvantages of current controlled release containers would therefore be desirable.

SUMMARY

This section provides a general summary of the disclosure, and is not a comprehensive disclosure of its full scope or all of its features.

The present teachings provide for a controlled release container including a dispensing tip and a base. The base includes a flexible diaphragm movable between a relaxed position and a depressed position. In the depressed position the flexible diaphragm reduces an interior volume of the container.

The present teachings provide for controlled release containers including various advantages, such as, but not limited to, the following: (1) a polymeric (plastic) container; (2) a dispensing portion formed during blow molding to provide a one-piece container with a dispensing portion integral with the container design; (3) a container that is less costly to manufacture, such as due to fewer components as compared to other controlled dispensing containers; (4) a dispensing diaphragm that can be activated with a single finger (or single thumb) at a base of the container; (5) finger or thumb placement at the base of the container to create an intuitive natural provider of stability during dispensing; (6) a dispensing diaphragm that can be activated with a force of less than 10 lbs.; (7) a diaphragm configured such that upon being depressed the diaphragm creates a pressure within the container dispensing a fixed amount of product; and (8) a container design in which dispensing and holding thereof is improved, such as due to the base being depressed.

The containers according to the present teachings provide for a droplet volume that is controlled by the design configuration of the container tip. The base of the container can also be optimized to create one drop per depress, or multiple drops per depress. Depressing the container bottom to deposit a droplet provides greater control over where the drop is dispensed, as compared to squeezing from the sides for example.

The containers according to the present teachings are advantageously configured such that there are no separate pieces to manufacture, store, or lose, which would prevent the container from functioning properly. The base diaphragm of the containers can be sized, shaped, and/or configured in any suitable manner to provide a customized and fixed dosage amount that is repeatable between dosings. The base diaphragm can also be sized, shaped, and/or configured in any suitable manner to modify and set the force required to depress the diaphragm and dispense a predetermined dosage amount. Material distribution at the base can be manipulated to change the force required to dispense the dose. To provide additional control of the dispensing amount, additional features can be added to the container, such as tips and orifices.

The sidewalls of the containers according to the present teachings generally have a greater rigidity as compared to a base at the diaphragm, which facilitates depressing the diaphragm. For example, a ratio of container sidewall thickness to base thickness can be between 1.5:1 to 3:1 without supporting geometry. The ratio can be less than 1.5:1 with supporting geometry, such as sidewall ribs. The thickness of the material at the diaphragm can be any suitable thickness to facilitate depressing of the diaphragm, such as between 0.009" and 0.018" inches. The actuation force of the diaphragm can be any suitable force, such as under ten pounds. The container finish can be any suitable size, such as between 10 mm and 33 mm. The dosing amount can be controlled by design of the base, with different designs configured to dispense different amounts. For example, based on the base design dosing amounts of about 0.05 ml. to about 2.5 ml. can be deposited.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 illustrates a container according to the present teachings, as well as a dispensing tip and a closure for the container;

FIG. 2 is a cross-sectional view of a container base according to the present teachings;

FIG. 20 is a side view of another container according to the present teachings;

FIG. 21 is a side view of yet another container according to the present teachings;

FIG. 22 is a side view of still another container according to the present teachings;

FIG. 23 is a side view of an additional container according to the present teachings;

FIG. 24 is a cross-sectional view of another container according to the present teachings;

Figure 29:
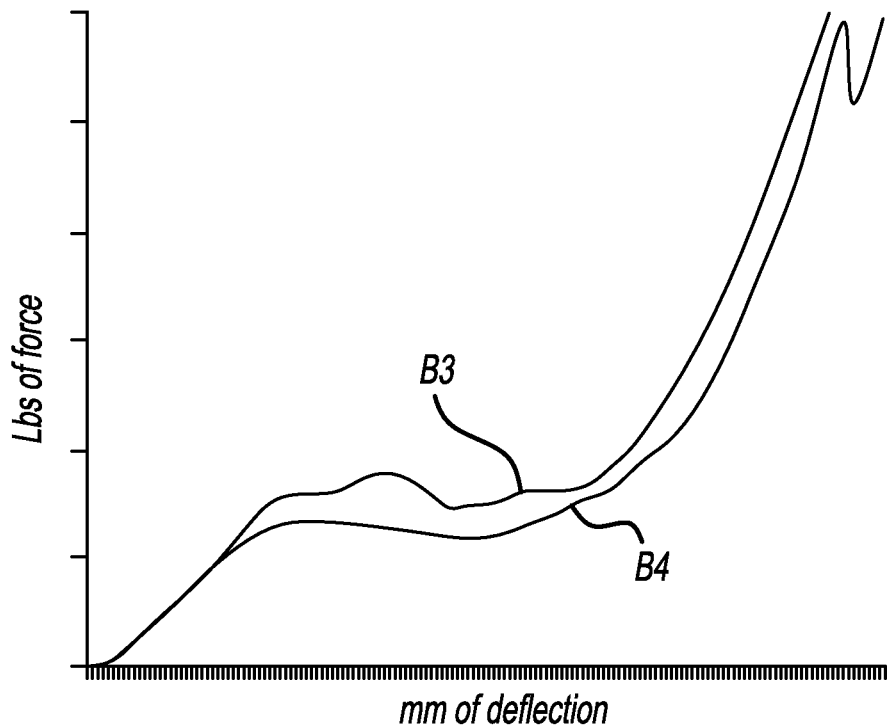
Figure 30:
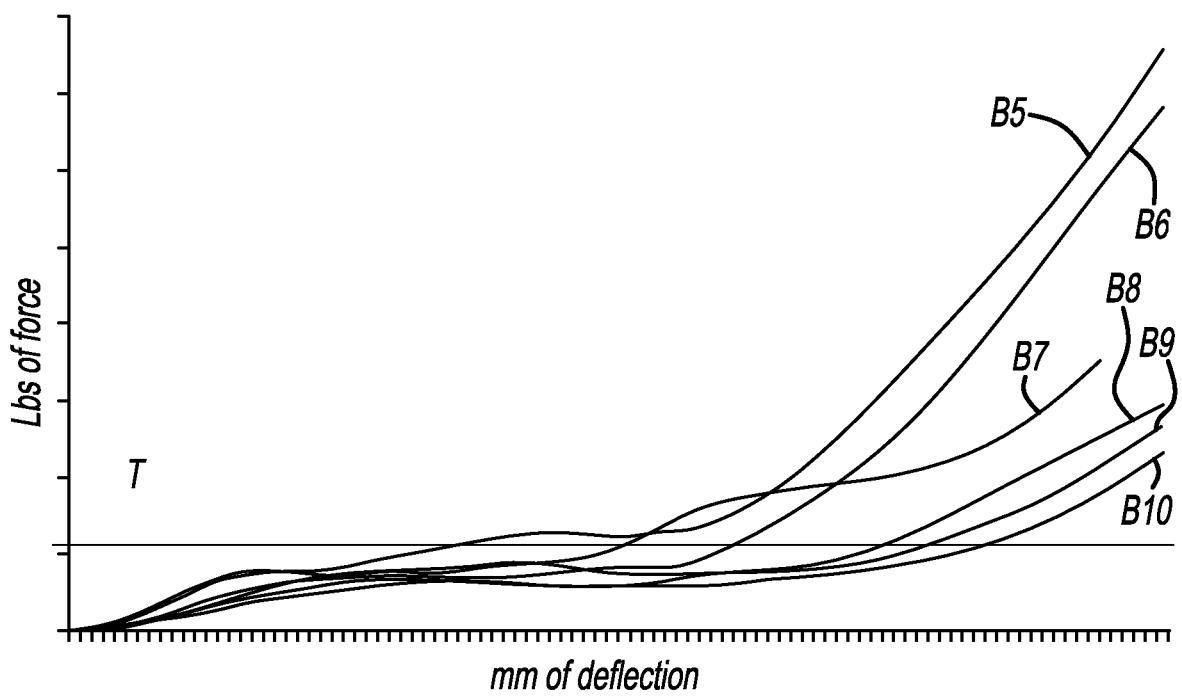

FIG. 29 is a graph showing that inclusion of a base surface feature, such as a center pushup portion, on a container base according to the present teachings provides for a more consistent and controlled dispensing of dosages as compared to container bases according to the present teachings without a center pushup portion; and FIG. 30 is a graph showing that containers according to the present teachings having straight walls have a higher activation force and a smaller dispense amount before high resistance as compared to containers according to the present teachings with tapered sidewalls.

Corresponding reference numerals indicate corresponding parts throughout the several views of the drawings.

DETAILED DESCRIPTION

Example embodiments will now be described more fully with reference to the accompanying drawings.

With initial reference to FIG. 1, an exemplary container according to the present teachings is generally illustrated at reference numeral 10. The container 10 can have any suitable capacity, such as 15 ml. The container 10 generally includes a first end 12 and a second end 14 at opposite ends of the container 10. A longitudinal axis A of the container 10 extends generally through an axial center of the container 10 from the first end 12 to the second end 14. At the first end 12, an aperture or opening 20 of the container 10 is defined by a finish 22 of the container 10. Extending from an outer periphery of the finish 22 are threads 24. Extending from the finish 22 towards the second end 14 is a neck portion 26 of the container 10. The neck portion 26 extends generally linearly to a shoulder portion 28 of the container 10. The shoulder portion 28 generally curves outward from a longitudinal axis A of the container 10 as the shoulder 28 extends from the neck 26 in the direction of the second end 14.

The container 10 further includes a body portion 30 extending from the shoulder 28 towards the second end 14. The body 30 includes a sidewall 32, which in the exemplary container 10 is cylindrical and extends generally linearly from the shoulder 28 towards the second end 14 such that the sidewall 32 extends generally parallel to the longitudinal axis A. The sidewall 32 extends from the shoulder 28 generally to a standing surface 34 of a base 110A of the container 10. Standing surface 34 is a surface of the container 10 that when seated on a planar surface extending generally perpendicular to the longitudinal axis A supports the container 10 in an upright position, as illustrated in FIG. 1.

The container 10 is configured to couple with any suitable dispensing tip at the finish 22, such as the dispensing tip 40 of FIG. 1. The dispensing tip 40 generally includes a tip base 42 having any suitable coupling member for coupling with the container 10, such as an annular flange 44 as illustrated. The dispensing tip 40 further includes a nozzle 46 defining an opening 48 through which any suitable substance stored within the container 10 can be dispensed. A support ring 50 is between the tip base 42 and the nozzle 46, and extends outward beyond each of the tip base 42 and the nozzle 46.

The dispensing tip 40 can be secured to the container 10 in any suitable manner. For example, the tip base 42 can be inserted through the aperture or opening 20 into the finish 22, where the annular flange 44 can cooperate with any suitable structure of the finish 22, such as an annular recess defined within the finish 22. The dispensing tip 40 can thus be depressed into the finish 22 until the flange 44 locks into the finish 22 at which point the support ring 50 will be generally coplanar with the aperture or opening 20 at the first end 12 in order to sit within the finish 22 in a position that is generally coplanar with the first end 12. A closure 52 is provided as generally a cap for the dispensing tip 40 and the container 10 in general. The closure 52 is sized and shaped to be seated over the dispensing tip 40 such that internal threads 54 of the closure 52 cooperate with the threads 24 of the finish 22 in order to secure the closure 52 to the finish 22 and over the dispensing tip 40.

Figure 3:
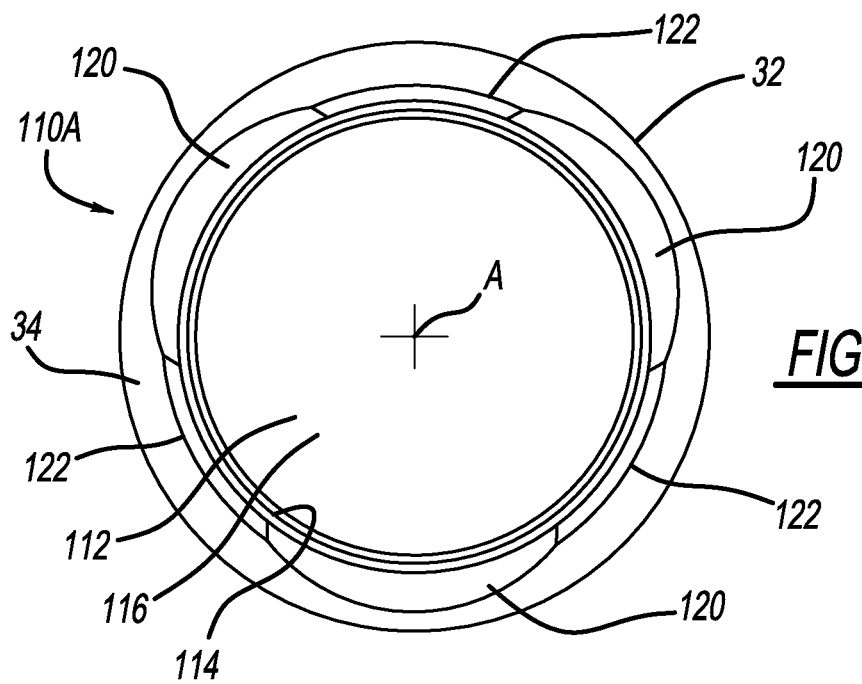
FIG. 3 is a plan view of the container base of FIG. 2.

With continued reference to FIG. 1, and additional reference to FIGS. 2 and 3, the base 110A of the container 10 will now be further described. The base 110A includes a flexible diaphragm 112. The flexible diaphragm 112 includes an outer diaphragm portion 114 and an inner diaphragm portion 116. The outer diaphragm portion 114 extends generally from the standing surface 34 to a transitional radius or hinge point 118, which is between the outer diaphragm portion 114 and the inner diaphragm portion 116. The longitudinal axis A extends generally through a center of the inner diaphragm portion 116.

The inner diaphragm portion 116 is movable between an initial relaxed position at which the inner diaphragm 116 has a convex, relaxed initial radius $R_i$, and a depressed position at which the inner diaphragm portion 116 has a depressed radius $R_d$. The inner diaphragm portion 116 can be moved from the relaxed position to the depressed position in any suitable manner, such as with a user's index finger or other finger or thumb. To facilitate grasping of the container 10 at the base 110A, a plurality of feet 120 and recesses 122 can be included, as illustrated in FIGS. 2 and 3. Each of the recesses 122 are arranged generally opposite to different feet 120 about an outer circumference of the base 110A, as illustrated in FIG. 3 in particular. The recess 122 generally provide additional clearance for the user's finger or thumb allowing the user to more readily insert his or her finger or thumb into the base 110A and in contact with the inner diaphragm 116.

The base 110A is sized and shaped such that upon depressing the diaphragm 112 to move the diaphragm 112 from the relaxed position to the depressed position in which the diaphragm 112 has the depressed radius $R_d$, a volume $V_d$ is displaced and a corresponding volume of material stored within the container 10 is dispensed from within the container 10 through the opening 48 of the dispensing tip 40. The amount of material dispensed from within the container 10 is thus directly proportional to the size of the displaced volume $V_d$, and thus the amount of material dispensed can be controlled by varying the displaced volume $V_d$. After the diaphragm 112 is moved to the depressed radius $R_d$, and the material is dispensed from within the container 10, the diaphragm 112 is sized and shaped to automatically return to the initial radius $R_i$.

Figure 28:
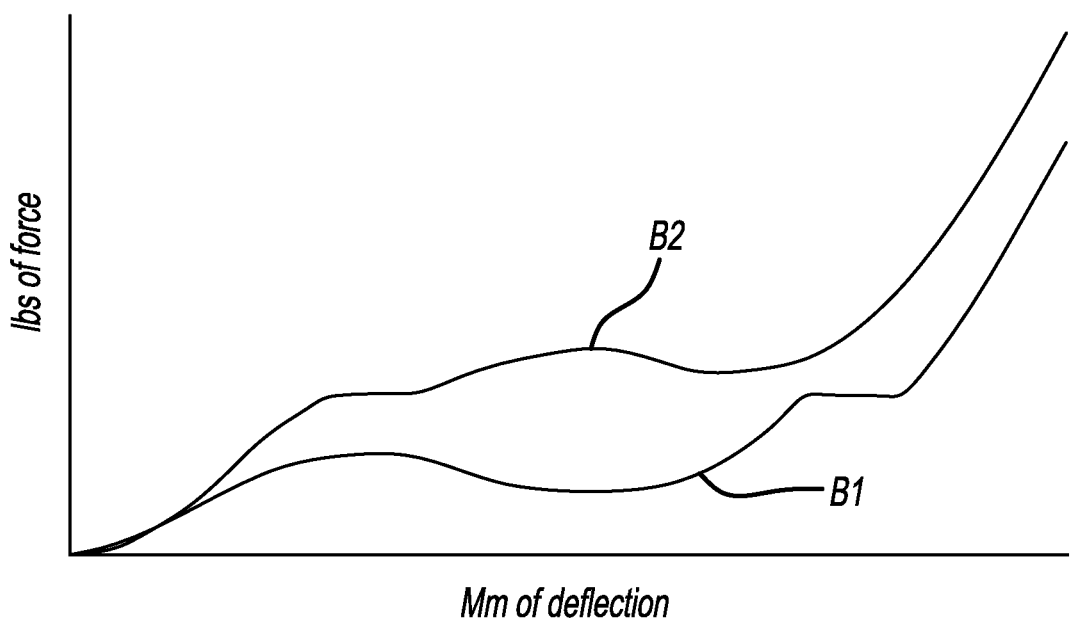
FIG. 28 is a graph illustrating that the amount of force required to depress container bases according to the present teachings is directly proportional to the material thicknesses of the container bases according to the present teachings.

To facilitate actuation of the diaphragm 112 from the relaxed position to the depressed position, the diaphragm 112 has a thickness that can be thinner than a thickness of the sidewall 32 of the body 30. For example, the inner diaphragm portion 116 can include a thickness $T_b$ that is less than a thickness $T_w$ of the sidewall 32. The thickness $T_w$ can be 1.5 to 3 times greater than the thickness $T_b$ of the inner diaphragm portion 116. Any suitable particular thicknesses can be provided. For example, the thickness $T_b$ can be between 0.009 inches and 0.018 inches. The actuation force required to move the diaphragm 112 from the relaxed initial radius $R_i$ to the depressed radius $R_d$ can be any suitable amount of actuation force, such as under 10 pounds. The force required to move the diaphragm 112 from the relaxed initial radius $R_i$ to the depressed radius $R_d$ is directly proportional to the thickness of the inner diaphragm portion 116. For example and as illustrated in FIG. 28, a base B1 according to the present teachings with a thickness of 0.010 inches can be depressed using less force as compared to a base B2 according to the present teachings having a thickness of 0.020 inches. The base 110A can be sized and shaped in any suitable manner to dispense any desired dosage amount, such as dosage amounts of 0.05 ml to about 2.5 ml of any suitable material, such as any suitable ophthalmic material when the container 10 is an ophthalmic container.

The container 10 can be manufactured in any suitable manner, such as blow molding, including stretch blow molding. For example, a preform of the container 10 can be placed in any suitable blow mold. An over-stroke unit can be positioned in a down position to assist with thinning of the base 110A. After the mold is closed, a counter-stretch operation is initiated, and then a stretch and blow process is performed. The base 110A is actuated with an over-stroke cylinder, and the stretch and blow process is completed. The counter-stretch rod is retracted, as is the over-stroke rod and base assembly. Finally, the mold is opened and the finished container 10 is removed from the mold. The container 10 can be made of any suitable material, such as polyethylene terephthalate (PET), any thermal plastic, or polypropylene, for example.

Figure 4:
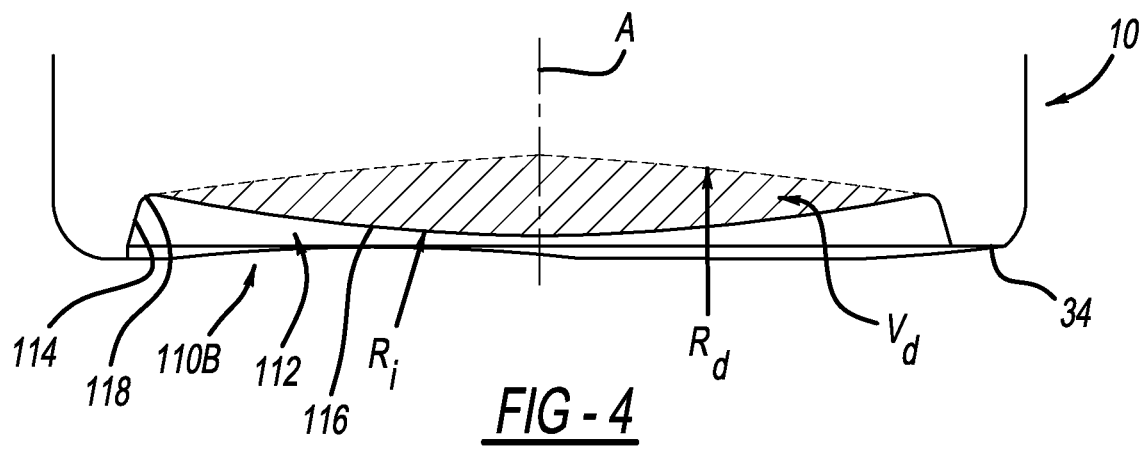
FIG. 4 is a cross-sectional view of another container base according to the present teachings.

Although the base 110A is illustrated as included with the container 10, any of the other containers described herein can include the base 110A, and the base 110A may be included with any other suitable container as well. Similarly, any of the other bases described herein can be included with the container 10. For example and with reference to FIG. 4, another container base 110B according to the present teachings is illustrated. The base 110B can be included with the container 10 of FIG. 1, or any other suitable container including the containers disclosed herein. The base 110B is similar to the base 110A, except that the volume displaced $V_d$ is smaller. As a result, the base 110B can be used in applications where the desired dosage of the material stored within the container 10 is less than the dosage desired when using the base 110A.

Figure 5:
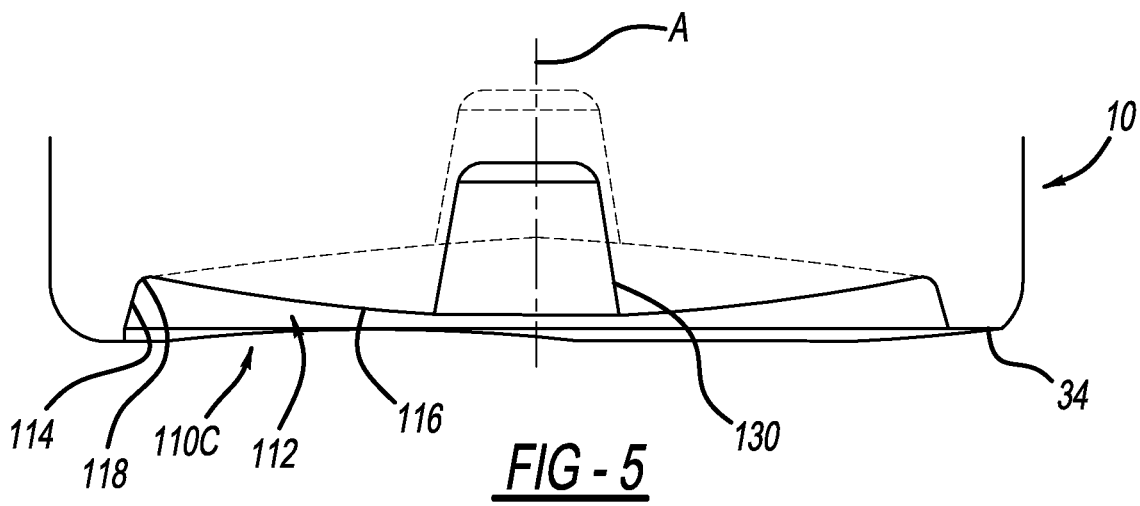
FIG. 5 is a cross-sectional view of still another container base according to the present teachings.

Another base that can be included with container 10, or any other suitable container including the other containers disclosed herein, is illustrated in FIG. 5 at reference numeral 110C. The base 110C is similar to the base 110A, but includes a recess or depression 130 at an axial center of the inner diaphragm portion 116. The depression 130 can have any suitable shape or configuration. For example, the depression 130 can be cone-shaped as illustrated in FIG. 5. The depression 130 provides the diaphragm 112 with an increased surface area, which allows the diaphragm 112 to be formed at a reduced thickness as compared to, for example, the diaphragms 110 of the bases 110A and 110B. U.S. Pat. No. 7,451,886 titled "Container Base Structure Responsive to Vacuum Related Forces," assigned to Amcor Limited explains further how the diaphragm 112 can be formed with a decreased thickness due to the presence of the depression 130, and is incorporated by reference herein.

Figure 6:
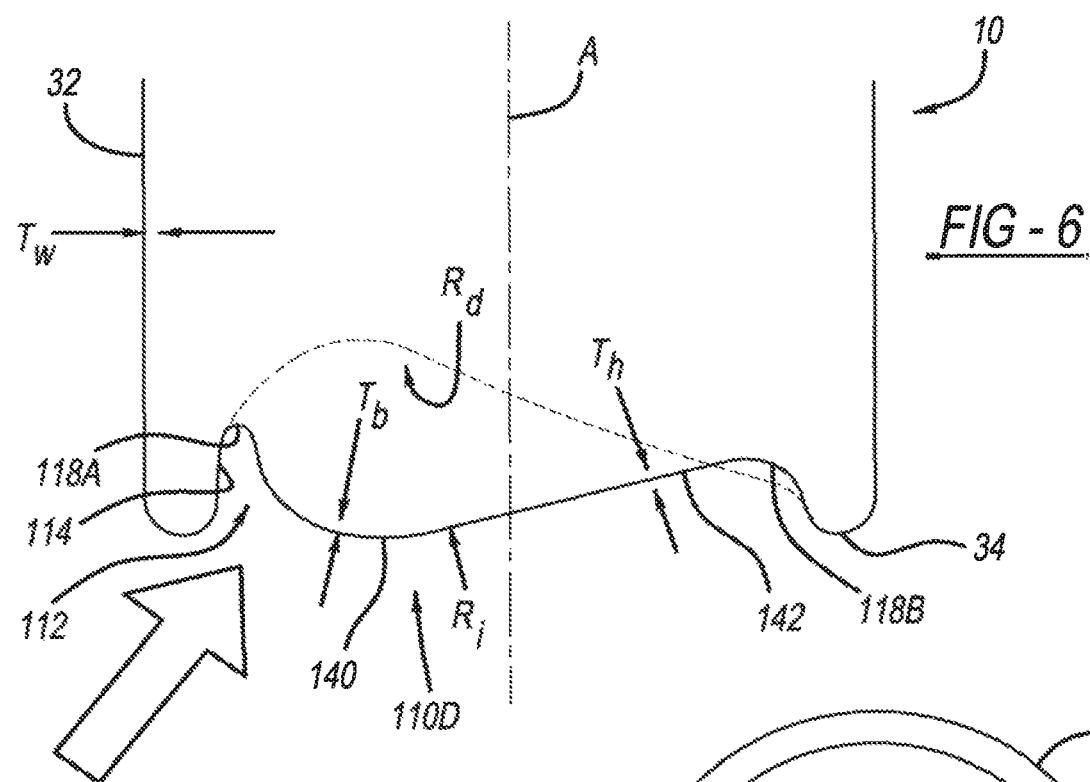
FIG. 6 is a cross-sectional view of still another container base according to the present teachings.

FIG. 6 illustrates another base according to the present teachings at reference numeral 110D. The base 110D can be included with the container 10, or any other suitable container including the containers disclosed herein. The base 110D includes the diaphragm 112 configured to have a button portion 140 and a hinge portion 142. The button portion 140 is proximate to a first portion 118A of the transitional radius 118, and the hinge portion 142 is proximate to a second portion 118B of the transitional radius 118. The first portion 118A has a smaller radius of curvature as compared to the second portion 118B. The button portion 140 is offset from the longitudinal axis A generally between the longitudinal axis A and the first portion 118A of the transitional radius 118. The hinge portion 142 is generally between the longitudinal axis A and the second portion 118B of the transitional radius 118. The hinge portion 142 is generally linear, while the button portion 140 has an initial radius $R_i$ when in the relaxed initial position. Upon being depressed by a user, such as when a user applies a force with their finger or thumb in the direction of the arrow of FIG. 6, the button portion 140 is moved from the initial radius $R_i$ in which the button 140 has a generally convex shape, to the depressed radius $R_d$ in which the button portion 140 has a generally concave shape as viewed from an exterior of the base 110D. To facilitate actuation of the button portion 140 from the initial radius $R_i$ to the depressed radius $R_d$, the button portion 140 can include a thickness $T_b$ that is thinner than a thickness $T_h$ of the hinge portion 142. The thickness $T_h$ of the hinge portion 142 can also be thinner than the thickness $T_w$ of the sidewall 32. The volume displaced by moving the base 110D to the depressed position is equal to a dosage amount of material that will be dispensed from the container 10, for example.

Figure 7:
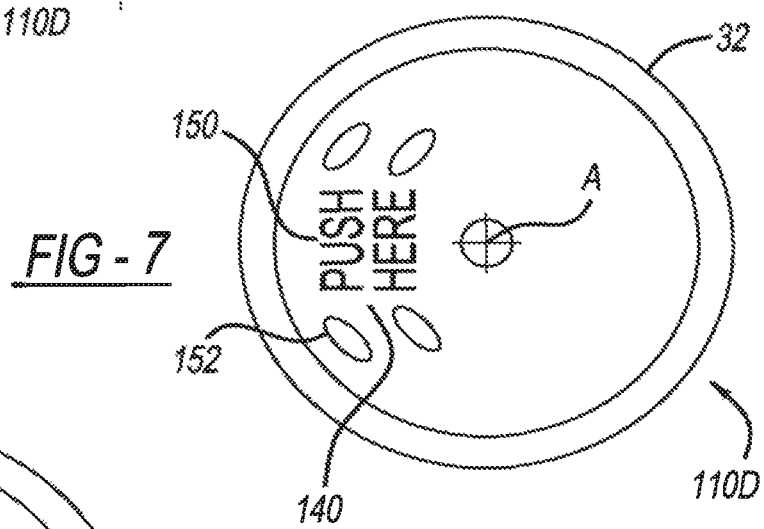
FIG. 7 is a plan view of an embodiment of the container base of FIG. 6.
Figure 8:
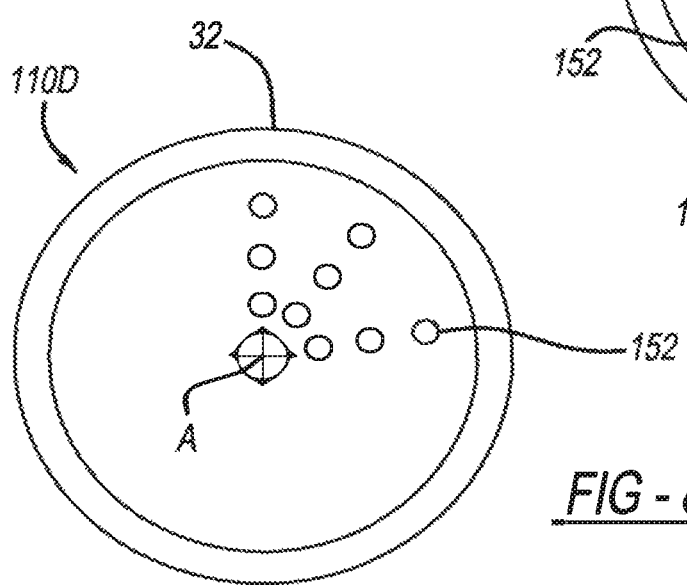
FIG. 8 is a plan view of another embodiment of the container base of FIG. 6.

To help a user locate the button portion 140, the base 110D can include any suitable indicator identifying where on the diaphragm 112 the button portion 140 is. For example and as illustrated in FIG. 7, any suitable indicator can be included such as a text indicator 150 (illustrated as "push here") or a surface feature indicator 152, such as raised or depressed dimples, can be included as illustrated in FIG. 7. With reference to FIG. 8, a plurality of indicators 152 in the form of dimples can be arranged such that they are aligned in rows extending outward from the longitudinal axis A at the button portion 140.

Figure 9:
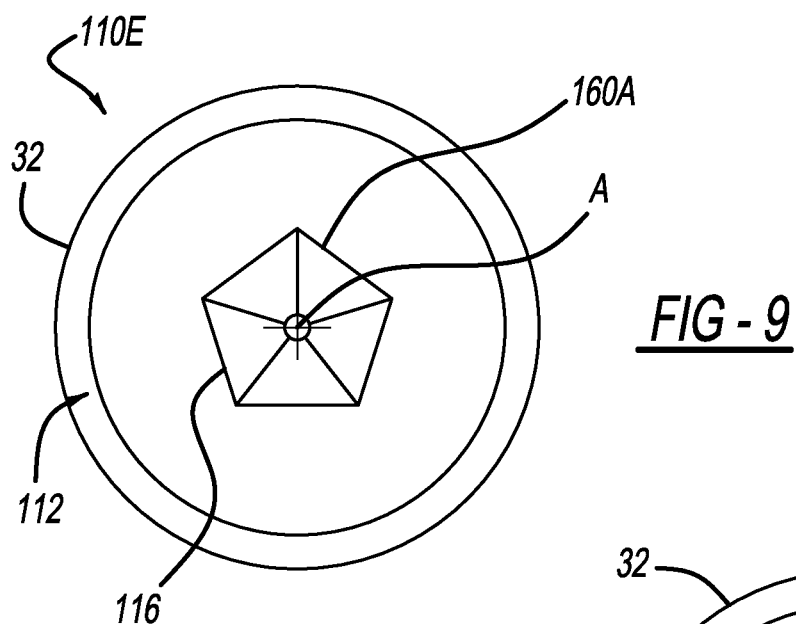
FIG. 9 is a plan view of a container base according to the present teachings.
Figure 10:
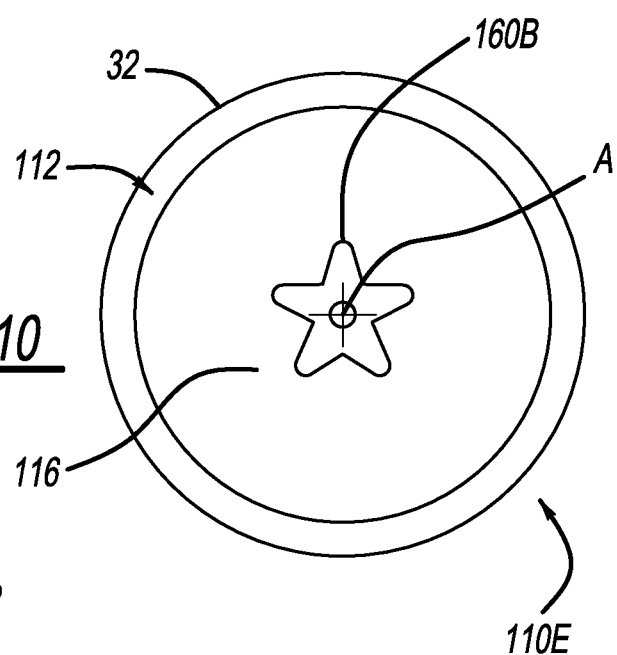
FIG. 10 is a plan view of an additional container base according to the present teachings.
Figure 11:
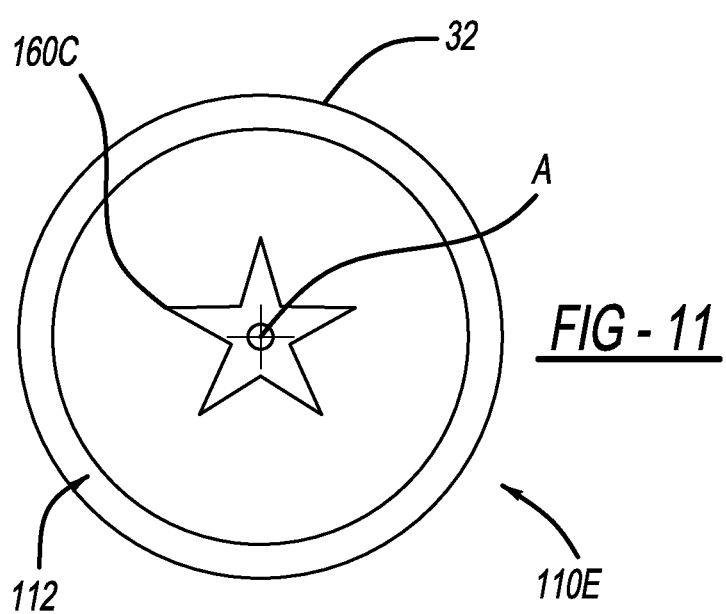
FIG. 11 is a plan view of still another container base according to the present teachings.

An additional base according to the present teachings is illustrated at FIG. 9 at reference numeral 110E. The base 110E includes a flexation enhancement feature 160A at the axial center of the diaphragm 112, and particularly at the inner diaphragm portion 116 such that the longitudinal axis A extends through a general center of the flexation enhancement feature 160A. The flexation enhancement feature 160A can be any suitable configuration of the inner diaphragm portion 116 configured to enhance flexing of the inner diaphragm portion 116 from the relaxed initial radius $R_i$ to the depressed radius $R_d$. For example, and as illustrated in FIG. 9, the flexation enhancement feature 160A can be shaped as a pentagon. With reference to FIG. 10, the present teachings further provide for a flexation enhancement feature 160B in the form of a five-pointed star with rounded end points. With reference to FIG. 11, an additional exemplary flexation enhancement feature is illustrated at reference numeral 160C in the form of a five-pointed star having pointed ends.

Figure 12:
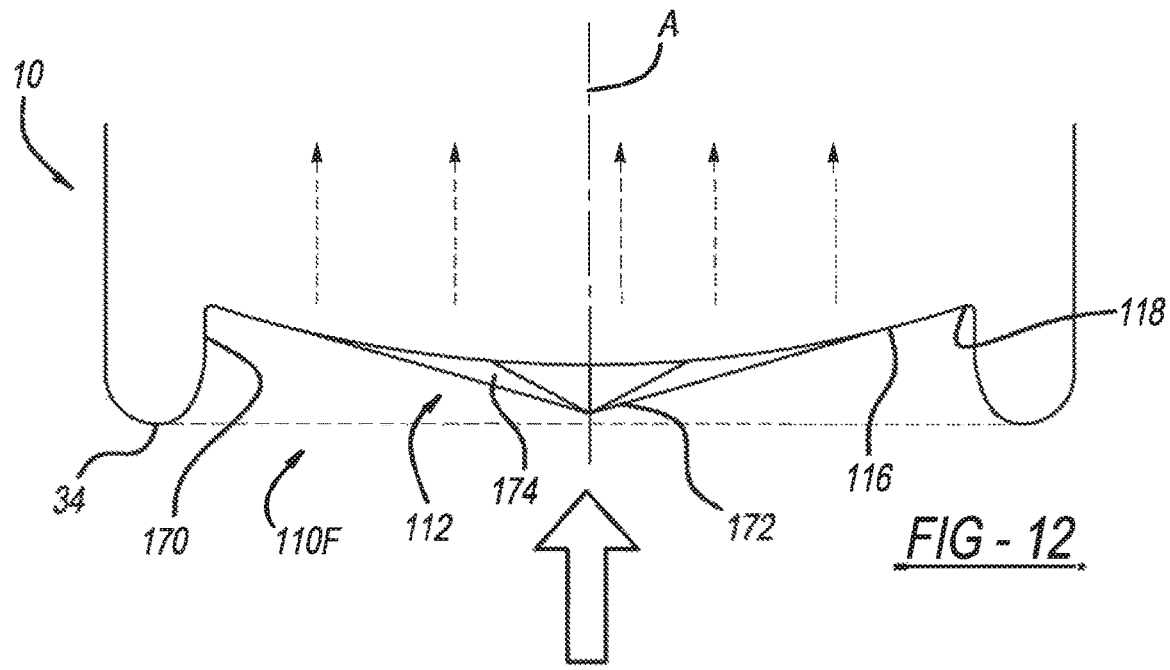
FIG. 12 illustrates another container base according to the present teachings.

FIG. 12 illustrates another base according to the present teachings at reference numeral 110F. The base 110F can be included with the container 10, or any other suitable container such as the other containers disclosed herein. The base 110F includes an inner sidewall 170 having at least a portion that extends generally parallel to the longitudinal axis A. A center portion 172 of the diaphragm 112 includes a plurality of panels 174 extending generally outward from the longitudinal axis A. The panels 174 extend furthest from the inner diaphragm portion 116 at the longitudinal axis A, and gradually taper towards the inner diaphragm portion 116 along the lengths thereof. Any suitable number of panels 174 can be provided in any suitable shape. The panels 174 advantageously increase the flexible area of the diaphragm 112 and provide a levered surface for the user to press upon thereby allowing the user to more easily move the diaphragm 112 from the relaxed position illustrated in FIG. 12 to a depressed position by applying a reduced amount of force as compared to applications that do not include the center portion 172 with the panels 174. The volume displaced by moving the base 110F to the depressed position is equal to a dosage amount of material that will be dispensed from the container 10, for example.

Figure 13:
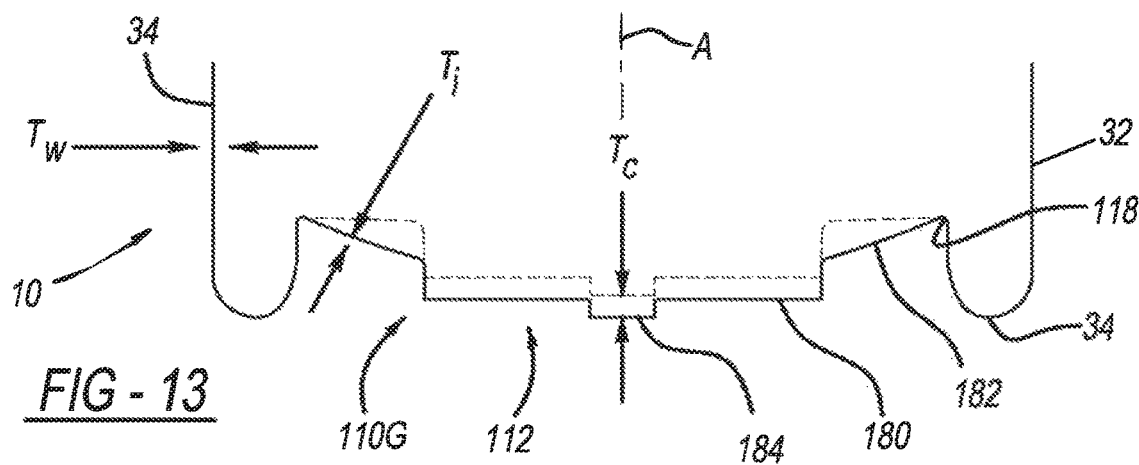
FIG. 13 is a cross-sectional view of an additional container base according to the present teachings.

FIG. 13 illustrates another container base according to the present teachings at reference number 110G. The container base 110G can be used with any of the containers described herein, as well as any other suitable container. The base 110G includes a center planar portion 180 between an intermediate portion 182 and a center tab 184. The intermediate portion 182 extends from hinged portion 118 towards the center planar portion 180, and is thus in between the hinged portion 118 and the center planar portion 180. The center planar portion 180 extends generally perpendicular to the longitudinal axis A of the container 10. The center tab 184 is at an axial center of the center planar portion 180 and extends outward beyond the center planar portion 180. The center tab 184 and the center planar portion 180 have a thickness $T_c$, which is greater than a thickness $T_i$ of the intermediate portion 182. The thickness $T_w$ of the sidewall 34 is greater than the thickness $T_i$ of the intermediate portion 182, as well as the thickness $T_c$ of the center tab 184 and the center planar portion 180. Making the thickness $T_c$ greater than the thickness $T_i$ provides the base 110G with a specific push area at the center tab 184 and the center planar portion 180. Upon depressing the base 110G at the center planar portion 180 and the center tab 184, the base 110G will hinge at hinged portion 118 to move from an initial relaxed position to a depressed position (illustrated in phantom in FIG. 13) to displace a volume equal to the distance that the center planar portion 180 and the center tab 184 are depressed. The volume displaced by moving the base 110G to the depressed position is equal to a dosage amount of material that will be dispensed from the container 10, for example.

Figure 14:
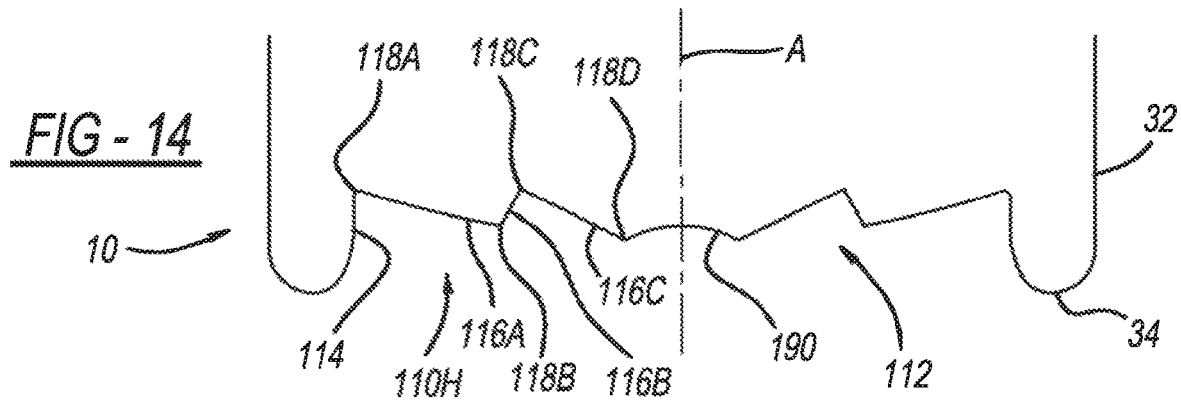
FIG. 14 is a cross-sectional view of yet another container base according to the present teachings.
Figure 15:
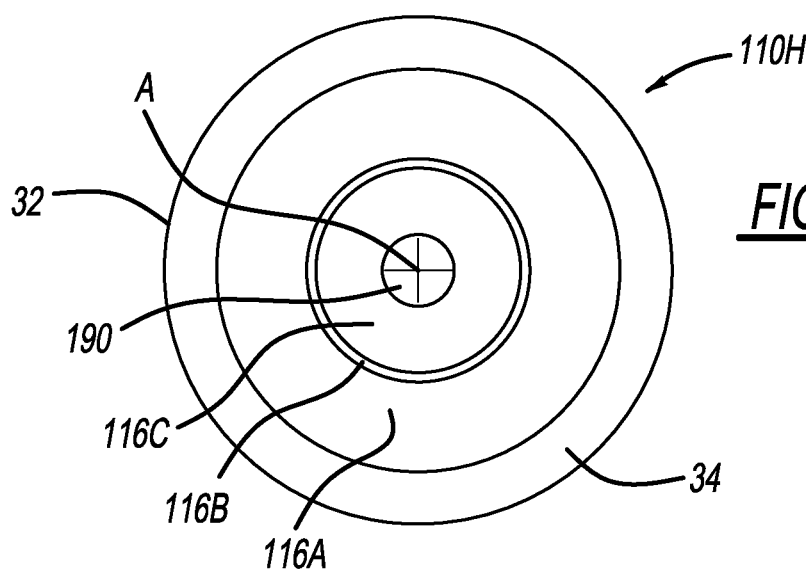
FIG. 15 is a plan view of the container base of FIG. 14.

Another base according to the present teachings is illustrated in FIGS. 14 and 15 at reference numeral 110H. The base 110H can be used with the container 10, or any other suitable container such as the other containers disclosed herein. The base 110H generally includes a diaphragm 112 having an outer portion 114 extending generally from the standing surface 34 to a first hinge point 118A. From the first hinge point 118A a first inner diaphragm portion 116A extends towards the longitudinal axis A to a second hinge point 118B. From the second hinge point 118B, a second inner diaphragm portion 116B extends inward in a direction towards the first end 12 of the container 10 to a third hinge point 118C. From the third hinge point 118C, a third inner diaphragm portion 116C extends to a fourth hinge point 118D and a center pushup portion 190. The center pushup portion 190 is at a center of the base 110G, and the longitudinal axis A extends through an axial center of the center pushup portion 190. Upon being depressed at the center pushup portion 190, or any areas of the base 110H proximate thereto, the base 110H will move inward to a depressed position by flexing at the first, second, third and fourth hinge points 118A, 118B, 118C, and 118D. The volume displaced by moving the base 110H to the depressed position is equal to a dosage amount of material that will be dispensed from the container 10, for example.

Figure 16:
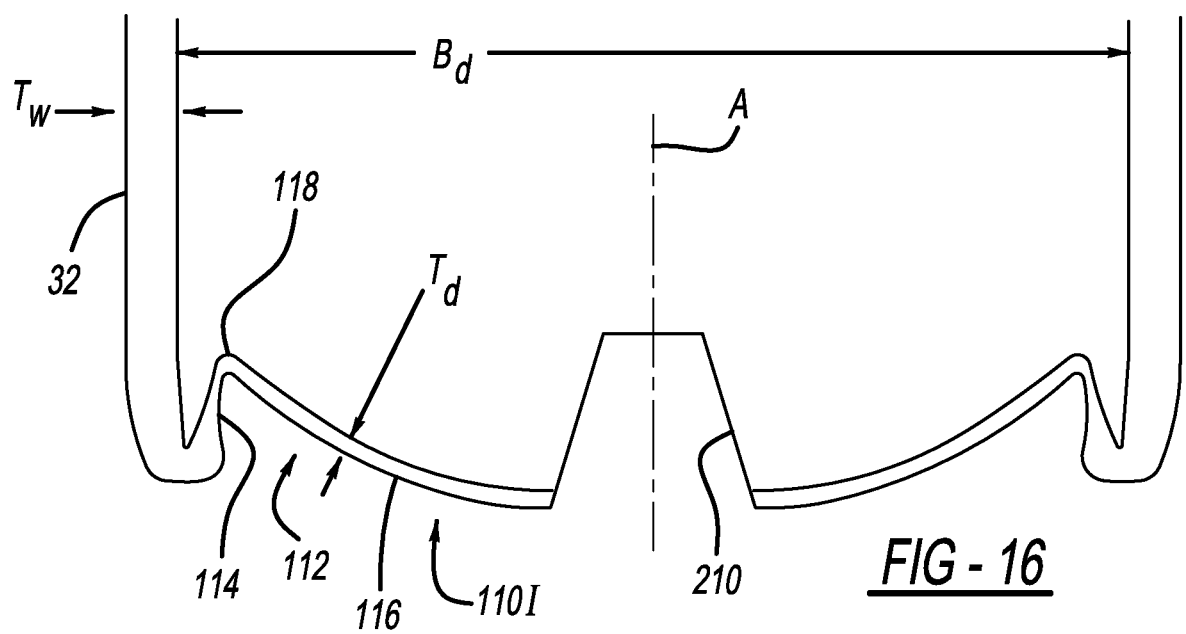
FIG. 16 is a cross-sectional view of an additional container base according to the present teachings.

FIG. 16 illustrates yet another container base according to the present teachings at reference numeral 110I. The base 110I includes the diaphragm 112 and transitional radius or hinge point 118 where outer diaphragm portion 114 transitions to inner diaphragm portion 116. At a center of the diaphragm 112 is a recess or depression 210, which may be of any suitable shape, such as cone-shaped. To facilitate movement of the base 110I from the illustrated initial relaxed position to the depressed position, the thickness $T_d$ of the inner diaphragm portion 116 is less than the thickness $T_w$ of the sidewall 32. The thickness $T_d$ can be any suitable thickness, such as 0.008"-0.020". The thickness $T_w$ of the sidewall 32 can be a minimum of 1.2 to 1.8 times greater than the thickness $T_d$ of the inner diaphragm portion 116, for example. As a diameter $B_d$ of the bottle or container 10 decreases, the magnitude that $T_w$ is greater than $T_d$ can increase. The volume displaced by moving the base 110I to the depressed position is equal to a dosage amount of material that will be dispensed from the container 10, for example.

Figure 17:
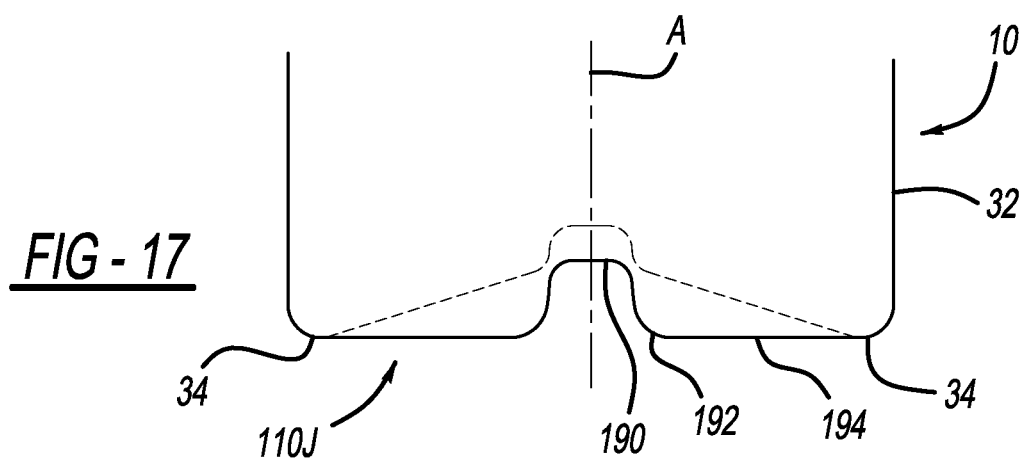
FIG. 17 is a cross-sectional view of an additional container base according to the present teachings.

An additional container base according to the present teachings is illustrated in FIG. 17 at reference numeral 110J. The base 110J can be included with the container 10, or any other suitable container including the containers disclosed herein. The base 110J generally includes a center pushup portion 190 at a center of the base 110J. The longitudinal axis 190 extends through an axial center of the center pushup portion 190. A hinge point 192 connects the center pushup portion 190 to an intermediate portion 194, which extends to the standing surface 34. The intermediate portion 194 can itself be a standing surface when the base 110J is in the initial relaxed position at which the intermediate portion 194 extends generally perpendicular to the longitudinal axis A. Upon being depressed by the user, the base 110J moves to the position of FIG. 17 illustrated in phantom, at which the center pushup portion 190 is moved inward along the longitudinal axis A and the intermediate portion 194 is non-orthogonal to the longitudinal axis A. The volume displaced by moving the base 110J to the depressed position is equal to a dosage amount of material that will be dispensed from the container 10, for example. The base 110J can be a Powerstrap™ base, such as any of the bases disclosed in WIPO Publication WO 2013/033550 published on Mar. 7, 2013, which is titled "Lightweight Container Base" and is assigned to Amcor Limited of Victoria, Australia. The entire disclose of WO 2013/033550 is incorporated herein by reference.

Figure 18:
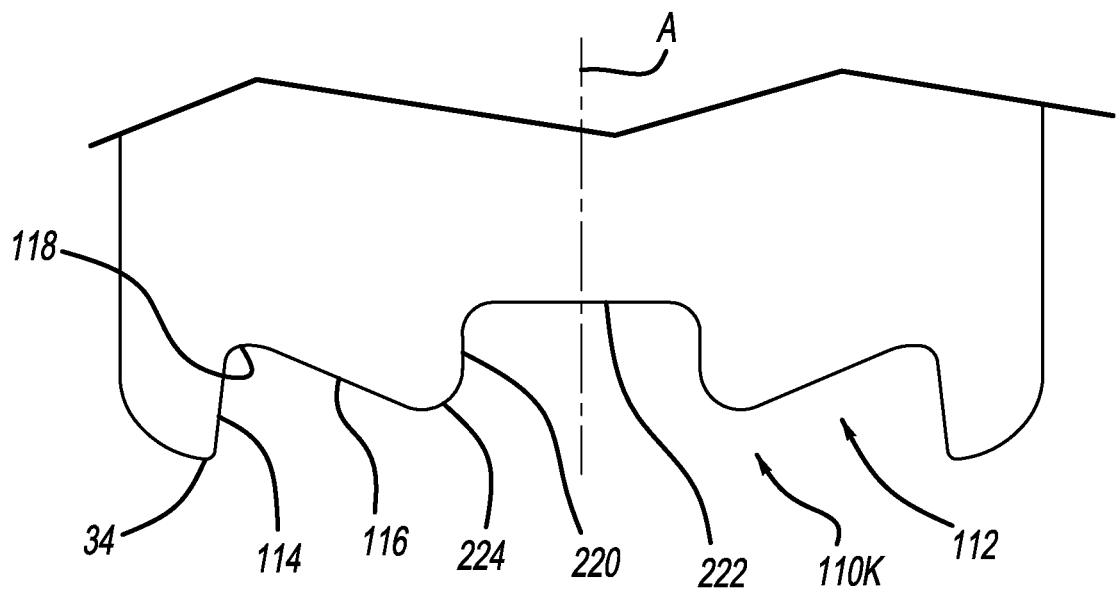
FIG. 18 is a cross-sectional view of still another container base according to the present teachings.

With reference to FIG. 18, another container base according to the present teachings is illustrated at reference numeral 110K. The base 110K includes outer diaphragm portion 114 extending from generally the standing surface 34 to transition radius 118. From transition radius 118 inner diaphragm portion 116 extends towards longitudinal axis A to isolation radius 224. Interfacial portion 222 extends from isolation radius 224 to center pushup portion 220. Longitudinal axis A extends through an axial center of the center pushup portion 222. The outer diaphragm portion 114 can extend inward from the standing surface 34 to any suitable depth, and can be angled towards the longitudinal axis A at any suitable angle to achieve a desired response when the base 110K is depressed, or extend parallel to the longitudinal axis A. For example, the outer diaphragm portion 114 can extend parallel to the longitudinal axis A or extend towards the longitudinal axis A at an angle of up to 45° relative to a line extending parallel to the longitudinal axis, such as about 15°. Upon pressing the base 110K, the base 110K will flex at the transition radius 118 and the isolation radius 224, the center pushup portion 220 will move along the longitudinal axis A, and the inner diaphragm portion 116 will move inward to move the base 110K from the illustrated relaxed position to a depressed position. The volume displaced by moving the base 110K to the depressed position is equal to a dosage amount of material that will be dispensed from the container 10, for example.

Figure 19:
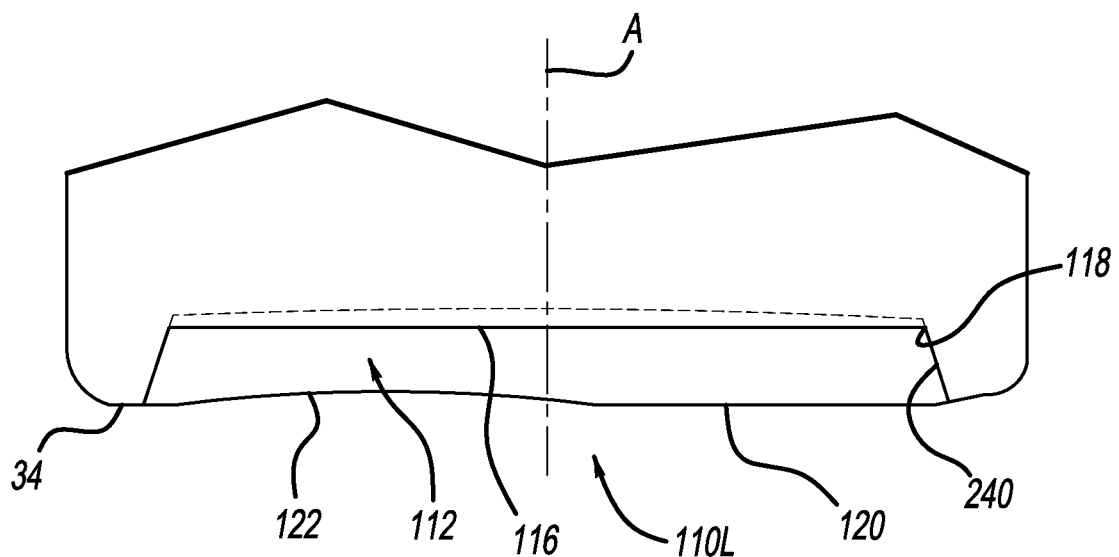
FIG. 19 is a cross-sectional view of another container base according to the present teachings.

Another container base 110L according to the present teachings is illustrated in FIG. 19. The container base 110L includes diaphragm 112 having a generally planar outer diaphragm portion 240 extending from standing surface 34. The outer diaphragm portion 240 extends to hinge portion 118, which is between the outer diaphragm portion 114 and inner diaphragm portion 116. Inner diaphragm portion 116 can be slightly bowed outward, or extend generally linearly across the base portion 110L, such that the inner diaphragm portion 116 extends generally perpendicular to the longitudinal axis A. The inner diaphragm portion 116 may be slightly bowed inward as well. Upon depressing the inner diaphragm portion 116, the base 110L will move inward along the longitudinal axis A to the depressed position illustrated in FIG. 19 in phantom. The volume displaced by moving the base 110L to the depressed position is equal to a dosage amount of material that will be dispensed from the container 10, for example.

FIG. 20 illustrates another container according to the present teachings at reference numeral 250. The container 250 can have any suitable capacity, such as 15 ml. The container 250 includes a sidewall 252, which extends between a shoulder portion 254 and standing surface 34 of the container 250. Extending from the shoulder portion 254 is a finish 256 including threads 258. The sidewall 252 is generally rounded and angled outward from longitudinal axis A of the container 250. The sidewall 252 generally tapers outward such that the sidewall 252 is closest to the longitudinal axis A at the shoulder 254, and furthest from the longitudinal axis A proximate to the standing surface 34. The container 250 includes a base 110M, which is similar to the base 110A described above. Thus the description of the base 110A set forth above also applies to the base 110M. The angled sidewall 252 provides the base 110M with a larger surface area, as compared to the base 110A for example in which the sidewall 32 is not angled outward from the longitudinal axis A. Due to the increased surface 110M, the thickness $T_b$ of the base 110M can be made smaller as compared to the thickness $T_b$ of the base 110A, which makes it easier to depress the base 110M to move the base 110M from the illustrated initial relaxed position to the depressed position to dispense a desired dosage. This is particularly important with smaller volume containers because the smaller the base area the harder it is to move the base, such as base 110M, from the initial relaxed position to the depressed position. The increased surface area at the base 110M provides the container 250 with a diameter at the base 110M of 1.05", for example, as compared to the diameter of the container 10 at the base 110A of about 0.803" for example. The container 250 can have any of the other bases disclosed herein in place of the base 110M.

Another container according to the present teachings is illustrated in FIG. 21 at reference number 260. The container 260 is generally similar to the container 250, and thus features in common with the container 250 are illustrated with like reference numbers. Unlike the container 250, the container 260 includes a flared base 110N having a foot portion 262. The foot portion 262 allows the surface area of the inner diaphragm portion 116 to be increased, which allows the base 110N to have a thickness $T_b$ that is even thinner than thickness $T_b$ of the base 110M. As discussed above, reducing the thickness $T_b$ makes it easier to depress the base 110N by requiring less force. The container 260 can have any suitable capacity, such as 15 ml. The container 260 can have any of the other bases disclosed herein in place of the base 110N.

FIG. 22 illustrates the container 260 including another base according to the present teachings at reference numeral 110O. The base 110O is generally the same as the base 110K (FIG. 18), but has an increased surface area because the sidewall 252 is tapered outward from the longitudinal axis A. The base 110O includes the foot portion 262 as well. The container 260 can have any of the other bases disclosed herein in place of the base 110O.

FIG. 23 illustrates another container according to the present teachings at reference numeral 270. The container 270 can have any suitable capacity, such as 15 ml. Similar to the container 250, the container 270 includes the finish 256, the threads 258, the shoulder 254, the sidewall 252, and the base 110M. Unlike the container 250, the sidewall 252 does not taper outward from the longitudinal axis A, but rather tapers inward at reference numeral 272. The container 270 also includes the foot portion 262, which allows the area of the base 110M to be increased. The foot portion 262 also increases the stability of the container 270, which can be particularly advantageous in view of the tapered portion 272. The thickness $T_b$ of the base 110M is less than the thickness $T_w$ of the sidewall 252 at the tapered portion 272 or any other portion of the sidewall 252. Although the container 270 is illustrated as including the container base 110M, the container 270 can have any other suitable base including any of the container bases disclosed herein.

Another container according to the present teachings is illustrated in FIG. 24 at reference numeral 280. The container 280 is generally similar to the container 10, but is larger. Like the container 10, the container 280 includes the aperture or opening 20, the finish 22, the threads 24, the neck 26, the body 30 including the sidewall 32, and the base 110A. The body 30 and the base 110A of the container 280 are larger than the body 30 and the base 110A of the container 10. Therefore, the container 280 has a larger capacity than the container 10. For example, the container 280 can have a capacity of 60 ml as compared to the container 10, which can have a capacity of 15 ml. Although the 60 ml container 280 is illustrated in FIG. 24 as having the base 110A, the container 280 can include any of the other bases disclosed herein.

Figures 25, 26:
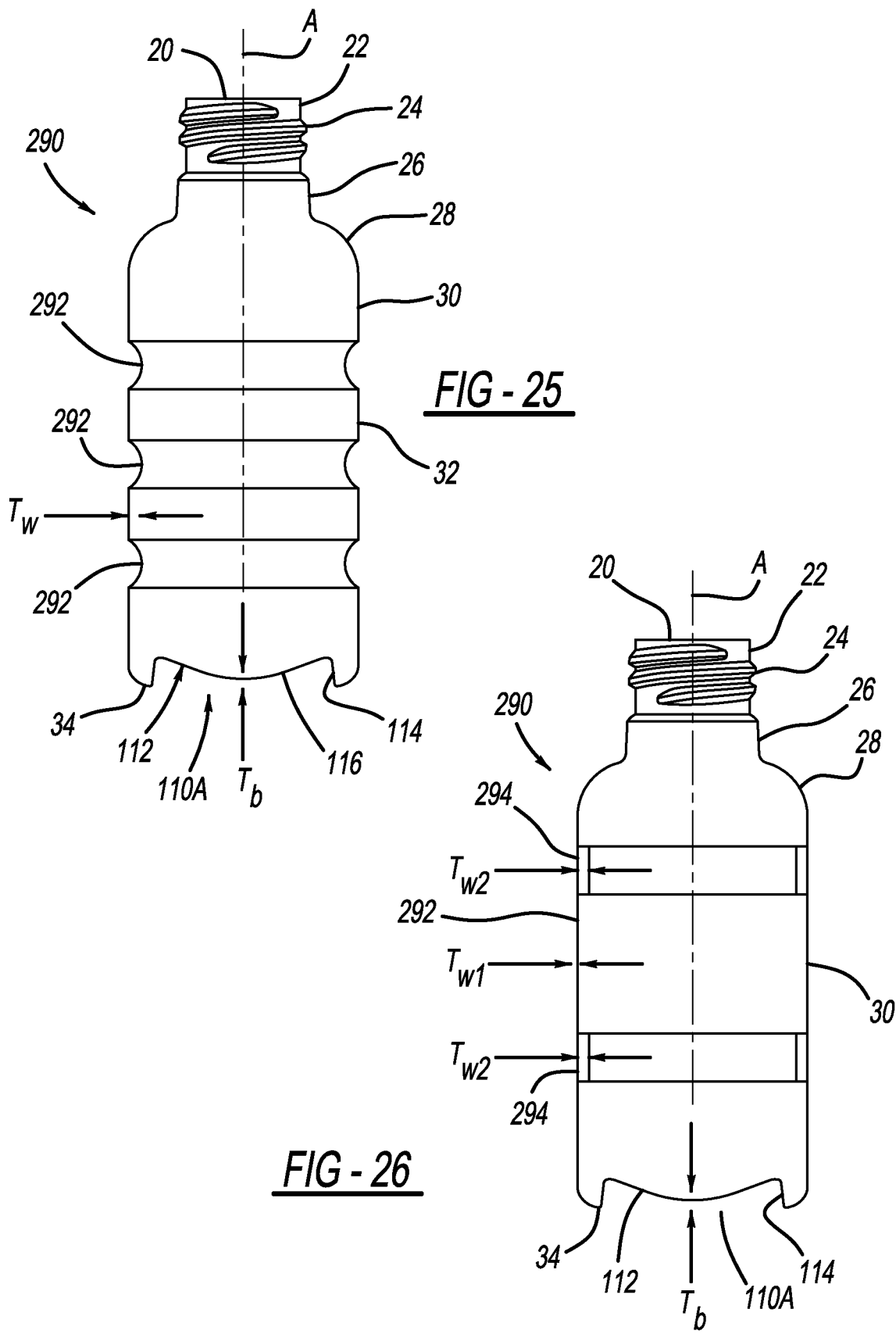
FIG. 25 is a side view of a container according to the present teachings.
FIG. 26 is a side view of yet an additional container according to the present teachings.

FIG. 25 illustrates yet another container according to the present teachings at reference numeral 290. The container 290 includes many of the same features of the container 10. The similar features are illustrated with the same reference numbers, and the description of the container 10 applies to the container 290 with respect to at least the similar features. The sidewall 32 of the container 290 includes ribs 292, which are generally annular recesses in the sidewall. Any suitable number of ribs 292 can be included, such as three as illustrated. The ribs 292 strengthen the sidewall 32, thereby allowing the sidewall 32 to be made thinner, which reduces the cost of the container 290. Thus, a ratio of the sidewall thickness $T_w$ to the base thickness $T_b$ for the container 290 including the ribs 292 is less than the ratio of a container, such as the container 10, that does not include the ribs 292. The ribs 292 can be included with any of the containers disclosed herein, and the container 290 can include any of the bases disclosed herein.

Instead of or in addition to the ribs 292, the container 290 can include any suitable stiffening features to reduce material usage and change wall thickness ratios, for example. With reference to FIG. 26, the container 290 can include one or more strengthening bands of increased material thickness, such as internal bands 294. The strengthening bands 294 are unitary with the container 290 and can extend annularly about the interior of the container 290 to strengthen the container 290. The strengthening bands 294 can have any suitable thickness, such as a thickness $T_w2$ that is greater than thickness $T_w1$ of the sidewall 30 where the strengthening bands 294 are not located. The strengthening bands 294 strengthen the sidewall 32, thereby allowing the sidewall 32 to be made thinner at areas that do not include the strengthening bands 294, which reduces the cost of the container 290. Thus, a ratio of the sidewall thickness $T_w$ to the base thickness $T_b$ for the container 290 including the strengthening bands 294 is less than the ratio of a container, such as the container 10, that does not include the strengthening bands 294. Any of the containers disclosed herein can include the strengthening bands 294 at any suitable location. While the container 290 is illustrated as including the base 110A, any other base can be included as well.

Figure 27:
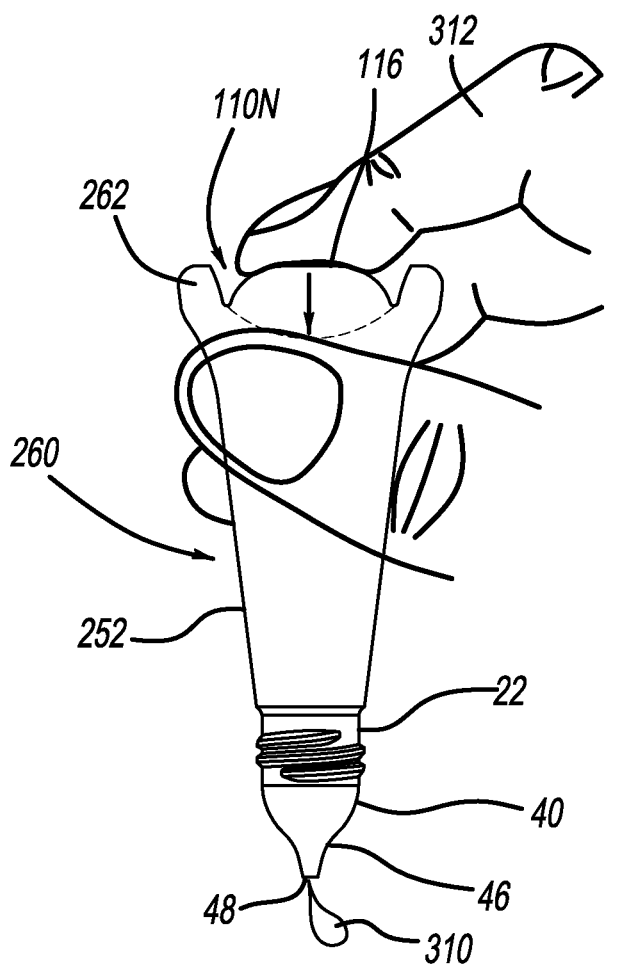
FIG. 27 illustrates actuation of a container base according to the present teachings to dispense a dosage of any suitable material.

FIG. 27 illustrates the container 260 including the dispensing tip 40 coupled thereto, and shows an exemplary manner of holding the container 260 for dispensing a dosage of any suitable material 310 stored in the container 260. As illustrated, the container 260 can be held upside down with a single hand proximate to the base 110N of the container 260, and the user's index finger 312 (or thumb) can be placed against the inner diaphragm portion 116. To dispense a dosage of the material 310 stored in the container 260, the index finger 312 (or thumb) depresses the inner diaphragm portion 116 to move the inner diaphragm portion 116 from the relaxed initial radius to the depressed radius illustrated in phantom. Depressing the inner diaphragm portion 116 creates an internal pressure in the container 260, which urges the material 310 within the container 260 to atmospheric pressure through the opening 48 of the tip 40. After the inner diaphragm portion 116 is depressed, the inner diaphragm portion 116 will return to the relaxed initial position so that the inner diaphragm portion 116 can again be depressed to dispense another dosage of the material 310. Any of the other containers disclosed herein can be operated in a similar manner.

Any suitable tip 40 can be used with the container 260, or any other suitable container. Viscosity of the material 310, dosage volume, activation, speed, and other factors determine an appropriate tip to diaphragm combination. A valve type tip can create a controlled opening and closing of the opening 48. After dispensing is complete, the base 110N will return to its initial neutral position, and air can be pulled back through the opening 48. The air can be returned through a filter, such as an antimicrobial filter, or other device of the container to prevent contamination.

Any of the containers according to the present teachings can also be used to withdraw or pull liquid out from within an area. For example and with respect to the container 10, the base 110A can be depressed, the tip 40 can be exposed to the liquid, and then the base 110A can be released to allow the base 110A to return to its neutral position. As the base 110A moves to its neutral position, a vacuum is created in the container 10 to pull liquid into the container 10 safely and easily.

FIG. 28 illustrates how wall thickness $T_w$ affects the amount of force needed to depress a base 110, such as the base 110C including the recess or depression 130. B1 illustrates the pounds of force needed to deflect the base 110C having a thickness of 0.010". B2 illustrates the pounds of force needed to deflect the base 110C having a thickness of 0.020". As illustrated in FIG. 28, less force is required to depress the thinner base B1 as compared to the thicker base B2. The ability to make the bases described herein thinner according to the present teachings is thus advantageous because doing so makes it easier to depress the bases to the depressed positions to dispense a given dosage of material 310.

FIG. 29 illustrates the amount of force needed to depress the base 110N (FIG. 21) not including the center pushup portion 222, as compared to the base 110O (FIG. 22) that does include the center pushup portion 222. Line B3 of FIG. 29 represents the amount of force required to depress the base 110N having a diameter of 1.05", and line B4 represents the amount of force required to depress the base 110O having a diameter of 1.05". A comparison of line B3 and B4 makes it clear that the base 110O including the center pushup portion 222 advantageously provides a more consistent and controlled response to force applied thereto as the base 110O is depressed.

FIG. 30 illustrates that containers according to the present teachings having straight sidewalls, such as the straight sidewall 32 of FIG. 1, have a higher activation force and a smaller dispense before high resistance. More specifically, FIG. 30 illustrates a target force T of 10 lbs. B5 represents container 10 including base 110A. B6-B8 represent container 10 including base 110K of FIG. 18. B9 represents container 260 including base 110N. B10 represents container 260 including base 110O. With respect to the container according to the present teachings represented at B6, for example, after the base thereof has been depressed to the depressed dispensing position and a predetermined amount of material has been dispensed, the force required to depress the base further increases quickly. This allows the targeted dispense amount to be met, and reduces the possibility of over-dispensing by further depressing the base after the predetermined amount of material has been dispensed.

The present teachings provide numerous advantages. For example and with respect to dispensing droplets, droplets may be controlled directly with the container and without the need for a secondary measuring device. For example, droplets of 0.05 ml per drop can be provided. Furthermore, droplet dispensing is effectuated by depressing a base 110 of the containers, which is more ergonomic as compared to squeezing the sides of the container as is required with existing containers.

With respect to dosing, a specific relatively large amount of liquid can be dispensed with accuracy, such as about 0.5 ml. to about 2.0 ml. Furthermore, neither an additional syringe nor a dropper with a bulb is required, which is in contrast to the prior art. The present teachings further provide design adjustability, thus permitting different amounts to be dispensed for different products. Liquid can be dispensed even if activation pressures are low, and base activation with polyethylene-terephthalate (PET) is made possible, which is in contrast to the current devices. Finally, dispensing can be provided by atomizing using an atomizing tip and depressing the container bottom.

The present teachings provide numerous improvements over current dispensing bottles, including but not limited to eye dropper squeeze bottles. For example, inversion and squeezing the sides of current bottles may result in too much liquid being deposited, and/or it can become difficult to accurately deposit the droplet in the eye. If one side of the container collapses more than the other as pressure is applied to the sides of the container by the user's fingers, the dropper tip is pulled to the side away from the blinking eye target. While some users may hold the container with a finger at the bottom of the container as a steadying influence, this system requires that it be done intuitively.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A controlled release container comprising:
a base including a flexible diaphragm, the diaphragm includes an outer portion surrounding an inner portion, the outer portion extends generally from a standing surface of the container to a hinge radius between the outer portion and the inner portion, a longitudinal axis of the container extends through a center of the inner portion;
the inner portion of the diaphragm includes a button portion adjacent a first portion of the hinge radius and a hinge portion adjacent a second portion of the hinge radius, the first portion has a smaller radius of curvature than the second portion;
the button portion protrudes further from the base than the hinge portion, the button portion is offset from the longitudinal axis and is between the longitudinal axis and the first portion of the hinge radius, the hinge portion is between the longitudinal axis and the second portion of the hinge radius;
the hinge portion is generally linear and the button portion has a relaxed convex radius when in a relaxed initial position, upon being depressed by a user the button portion is configured to move from the relaxed convex radius to a depressed concave shape as viewed from an exterior of the base;
when moved to the depressed concave shape the flexible diaphragm reduces an interior volume of the container to dispense a dosage amount of material stored within the container, the dosage amount directly corresponds to an internal volume of the container displaced by depressing the flexible diaphragm;
wherein the button portion includes a first thickness that is less than a second thickness of the hinge portion, the container includes a sidewall having a third thickness that is greater than both the first and the second thicknesses, and the second thickness is greater than the first thickness and less than the third thickness;
wherein the container is of unitary construction; and
wherein the container is formed by blow-molding.

2. The controlled release container of claim 1, wherein the flexible diaphragm is biased to return to the relaxed position after being moved to the depressed position.

3. The controlled release container of claim 1, wherein the container is selected from the group consisting of a dosing container, eyedropper, chemical dispenser, pharmaceutical dispenser, and food dispenser.

4. The controlled release container of claim 1, wherein the flexible diaphragm is thinner than a sidewall of the container.

5. The controlled release container of claim 1, wherein a sidewall of the container is at least 1.2 times thicker than the flexible diaphragm.

6. The controlled release container of claim 1, wherein the container includes at least one of polyethylene-terephthalate or polypropylene.

7. The controlled release container of claim 1, wherein the flexible diaphragm is configured to be moved from the relaxed position to the depressed position with a single finger or single thumb.

8. The controlled release container of claim 1, wherein a dispensing tip and the flexible diaphragm are configured to repeatedly dispense a predetermined fixed dosage each time the flexible diaphragm is moved from the relaxed position to the depressed position.

9. The controlled release container of claim 1, wherein the diaphragm is configured to invert from the relaxed convex radius to a depressed concave shape under external force to create a pressure in the container to dispense material stored in the container through a dispensing tip.

* * * * *